(12) United States Patent
Ninh (10) Patent No.: US 12,064,103 B2
(45) Date of Patent: Aug. 20, 2024

(54) KNOTLESS LABRAL REPAIR TECHNIQUES AND RELATED DEVICES

(71) Applicant: Christopher Ninh, Irvine, CA (US)

(72) Inventor: Christopher Ninh, Irvine, CA (US)

( * ) Notice: Subject to any disclaimer, the term of this patent is extended or adjusted under 35 U.S.C. 154(b) by 115 days.

(21) Appl. No.: 17/736,015

(22) Filed: May 3, 2022

(65) Prior Publication Data

US 2023/0190257 A1 Jun. 22, 2023

Related U.S. Application Data

(63) Continuation of application No. 17/553,670, filed on Dec. 16, 2021, now Pat. No. 11,344,290.

(51) Int. Cl.
*A61B 17/04* (2006.01)

(52) U.S. Cl.
CPC ...... *A61B 17/0401* (2013.01); *A61B 17/0485* (2013.01); *A61B 17/0487* (2013.01); *A61B 2017/0414* (2013.01)

(58) Field of Classification Search
CPC ............ A61B 17/0401; A61B 17/0485; A61B 17/0487; A61B 2017/0412; A61B 2017/0414; A61B 2017/044
See application file for complete search history.

(56) References Cited

U.S. PATENT DOCUMENTS

| | | |
|---|---|---|
| 8,118,836 B2 | 2/2012 | Denham et al. |
| 8,545,535 B2 | 10/2013 | Hirotsuka et al. |
| 8,652,172 B2 | 2/2014 | Denham et al. |
| 9,060,764 B2 | 6/2015 | Sengun |
| 9,295,460 B2 | 3/2016 | Hoof et al. |
| 9,421,007 B2 | 8/2016 | Brady et al. |
| 9,445,805 B2 | 9/2016 | Snell et al. |
| 9,808,242 B2 | 11/2017 | Ng et al. |
| 10,092,285 B2 | 10/2018 | Graul et al. |
| 10,111,652 B2 * | 10/2018 | Patel ................... A61B 17/0401 |
| 10,390,821 B2 | 8/2019 | Frank |
| 10,492,775 B2 | 12/2019 | Vijay et al. |
| 10,595,853 B2 | 3/2020 | Feezor et al. |
| 11,266,398 B2 * | 3/2022 | Sauer .................. A61B 17/062 |
| 2010/0160962 A1 | 6/2010 | Dreyfuss |
| 2013/0296934 A1 | 11/2013 | Sengun |
| 2014/0081322 A1 | 3/2014 | Sengun |
| 2014/0188163 A1 | 7/2014 | Sengun |
| 2014/0249577 A1 | 9/2014 | Pilgeram |
| 2014/0257382 A1 | 9/2014 | McCartney |

(Continued)

*Primary Examiner* — Phong Son H Dang
(74) *Attorney, Agent, or Firm* — Roland J. Tong (57) ABSTRACT

A suture anchor for use in a knotless, suture-first technique for securing soft tissue to bone comprises a proximal anchor body and a distal tip having an eyelet configured to receive an end of a repair suture. Internal locking elements on the distal tip and the proximal anchor body are provided for locking the tip and anchor body together when the suture anchor is implanted in a bone. A suture assembly for use in an alternate knotless technique comprises a suture anchor, a repair suture, and a shuttle suture. Both the repair suture and the shuttle suture rea looped at one end and straight at the other end. In the alternate technique, the loop and tail of the repair suture are manipulated to form a luggage tag configuration extending around the tissue, and the shuttle suture is used to tightly secure the luggage tag configuration and tissue against the bone.

5 Claims, 8 Drawing Sheets

(56) References Cited

U.S. PATENT DOCUMENTS

| | | |
|---|---|---|
| 2014/0277132 A1 | 9/2014 | Sengun |
| 2015/0164497 A1 | 6/2015 | Callison |
| 2017/0049432 A1 | 2/2017 | Dooney, Jr. |
| 2017/0049434 A1 | 2/2017 | Dooney, Jr. |
| 2017/0189007 A1 | 7/2017 | Burkhart |
| 2018/0221010 A1 | 8/2018 | Lund |
| 2019/0343507 A1 | 11/2019 | Chavan et al. |
| 2020/0022701 A1 | 1/2020 | Crook et al. |
| 2021/0186487 A1 | 6/2021 | Korman |
| 2021/0378653 A1 | 12/2021 | Dreyfuss |

* cited by examiner

KNOTLESS LABRAL REPAIR TECHNIQUES AND RELATED DEVICES

CROSS-REFERENCE TO RELATED APPLICATIONS

This application is a continuation of U.S. nonprovisional patent application Ser. No. 17/553,670, filed Dec. 16, 2021, the entire contents of which are incorporated herein by reference.

BACKGROUND OF THE INVENTION

1. Field of the Invention

The present disclosure relates in general to soft tissue repair surgery, and more particularly to surgical methods and devices for shoulder labral repair.

2. Background Art

Labral tears can occur as a result of sports injuries and other types of trauma, and can also be caused by aging, as the labrum becomes brittle over time. Minor tears can be treated with medication, physical therapy, and rest, but more severe injuries require surgery.

Labral surgery can be open or arthroscopic, and can be performed using knotted or knotless techniques. A typical knotted repair technique involves loading a suture having two free ends into a suture anchor and implanting the suture anchor in the glenoid bone in a location on one side of the torn labrum. After one end of the suture is passed between the labrum and the glenoid, the two ends are tied together to create a knot securing the labrum to the bone. In a knotless repair technique, the suture is passed through the labrum first, and then its two ends are fed into the distal end of a suture anchor before the suture anchor is implanted in the bone. After the suture anchor has been implanted, the suture ends are held in place by an interference fit between the suture anchor and the bone.

Knotless labral repair techniques are generally preferred to knotted techniques, but they can be problematic since they allow relative movement between the labrum and the suture. In addition, suture slippage can occur if the interference fit between a knotless suture anchor and the surrounding bone is not sufficiently tight, as is frequently the case in patients having diminished bone density due to age or disease.

These and other problems are addressed by this disclosure as summarized below.

SUMMARY OF THE INVENTION

In one aspect of the disclosure, a suture anchor for use in a knotless, suture-first technique for securing soft tissue to bone comprises a proximal anchor body and a distal tip having an eyelet configured to receive an end of a repair suture. The distal tip is detachably secured to the distal end of a driver shaft, and the proximal anchor body is mounted for longitudinal movement toward the distal tip. Internal locking elements on the distal tip and the proximal anchor body are provided for locking the tip and anchor body together when the suture anchor is implanted in a bone.

In one aspect of the disclosure, the internal locking elements comprise mating portions of a snap lock. The snap lock may comprise an annular groove or bead on a distal portion of the anchor body and an annular groove configured to receive the annular bead, or an annular bead configured to project into the annular groove.

In another aspect of the disclosure, the proximal anchor body may comprise an exterior wall including a plurality of annular ribs separated by annular channels.

In still another aspect of the disclosure, the driver shaft comprises an inner shaft and an outer shaft mounted for sliding movement relative to one another. The distal tip is configured to be detachably secured to the inner shaft, and the proximal anchor body is configured to be detachably secured to and slidable with the outer shaft.

In yet another aspect of the disclosure, the proximal anchor body may include a distal end defining a notch configured to align with the eyelet in the distal tip when the proximal anchor body is in a fully deployed position, the notch having a proximal end preventing proximal movement of a repair suture extending through the eyelet when the semicircular notch is aligned with the eyelet.

A suture assembly for use in an alternate technique for securing soft tissue to bone comprises a suture anchor, a repair suture, and a shuttle suture. The suture anchor has a first side, a second side, and a proximal end. The repair suture has a looped end and a tail, and is doubled on itself and positioned in the suture anchor such that its looped end extends out of the proximal end of the suture anchor on the first side thereof, and its tail extends out of the proximal end of the suture anchor on the second side thereof. The shuttle suture has a looped end and a tail, and is doubled on itself and positioned in the suture anchor such that its looped end extends out of the proximal end of the suture anchor on the second side thereof, and its tail extends out of the proximal end of the suture anchor on the second side thereof.

In another aspect of the disclosure, the loop of the repair suture is larger than the loop of the shuttle suture.

In still another aspect of the disclosure, the repair suture is thicker than the shuttle suture.

In yet another aspect of the disclosure, the repair suture has a thickness which varies from a maximum in the loop to a minimum in the tail.

A method for securing soft tissue to bone using the suture assembly disclosed above comprises inserting the suture assembly into a bone below and to one side of a detached tissue, passing the tail of the repair suture between the detached tissue and the bone, and passing the tail of the repair suture back over the detached tissue and through the loop of the repair suture to create a luggage tag configuration.

In one aspect of the disclosure, the method further includes locking the luggage tag configuration in place against the tissue by capturing the tail of the repair suture in an interference fit between the suture engagement feature and the inner wall of the suture anchor.

In one aspect of the disclosure, the method further includes passing the loop of the shuttle suture between the detached tissue and the bone; pulling the tail of the repair suture through the loop of the shuttle suture after the luggage tag configuration has been created; and pulling the tail of the shuttle suture to draw the tail of the repair suture down through the second side, up through the first side, and out through the proximal end on the first side of the suture anchor, thus tightening the luggage tag configuration against the tissue.

In another aspect of the disclosure, the detached tissue is a torn shoulder labrum and the bone is a glenoid bone.

In another aspect of the disclosure, the method comprises implanting a suture anchor into a bone below and to one side of the tissue, the suture anchor having been preloaded with a repair suture having a looped end and a tail; passing the tail of the repair suture between the detached tissue and the bone; passing the tail of the repair suture back over the detached tissue and through the loop of the repair suture to create a luggage tag construct; and locking the luggage tag configuration in place against the tissue.

In still another aspect of the method, the suture anchor includes an inner wall defining a cannulation, and a suture engagement feature extending across the cannulation, and locking the luggage tag configuration in place against the tissue comprises capturing the tail of the repair suture in an interference fit between the suture engagement feature and the inner wall.

In an alternative method, the suture anchor assembly comprises an all suture anchor wherein the repair suture and shuttle suture are embedded in a tube or sleeve that is configured to collapse in a longitudinal direction and expand in a radial direction and to exert a contact force on the surrounding bone when deployed, and locking the luggage tag configuration in place against the tissue comprises deploying the all suture anchor to exert the contact force against the surrounding bone.

DETAILED DESCRIPTION OF THE PREFERRED EMBODIMENT(S)

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1A:
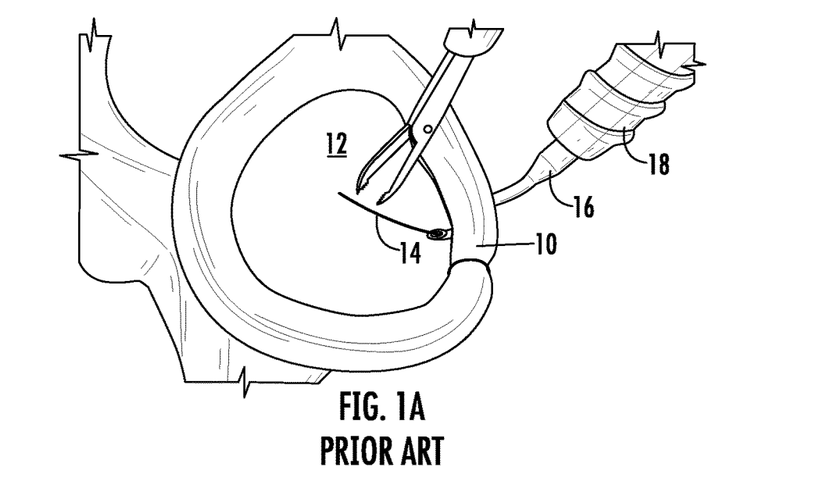
FIGS. 1A-E illustrate a prior art method of securing a torn shoulder labrum to a glenoid bone.
Figure 1B:
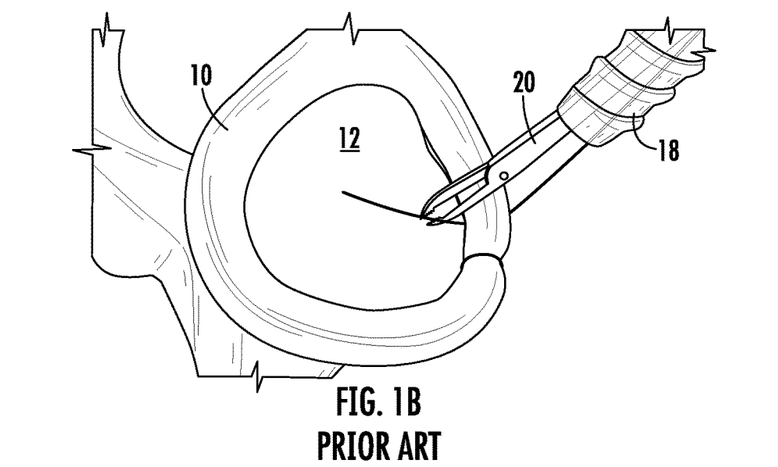
Figure 1C:
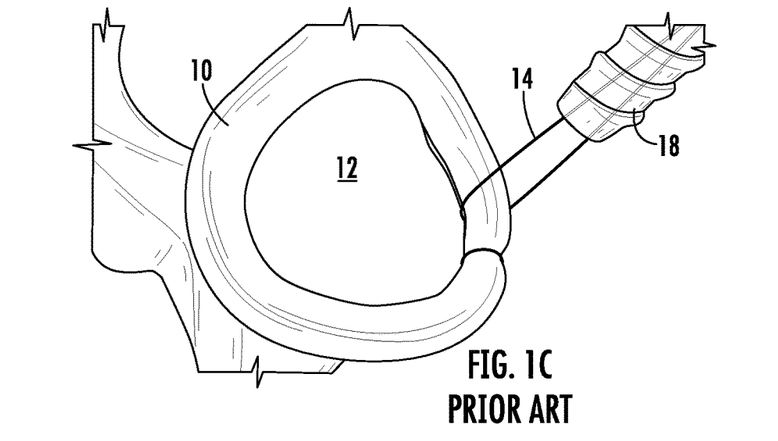
Figure 1D:
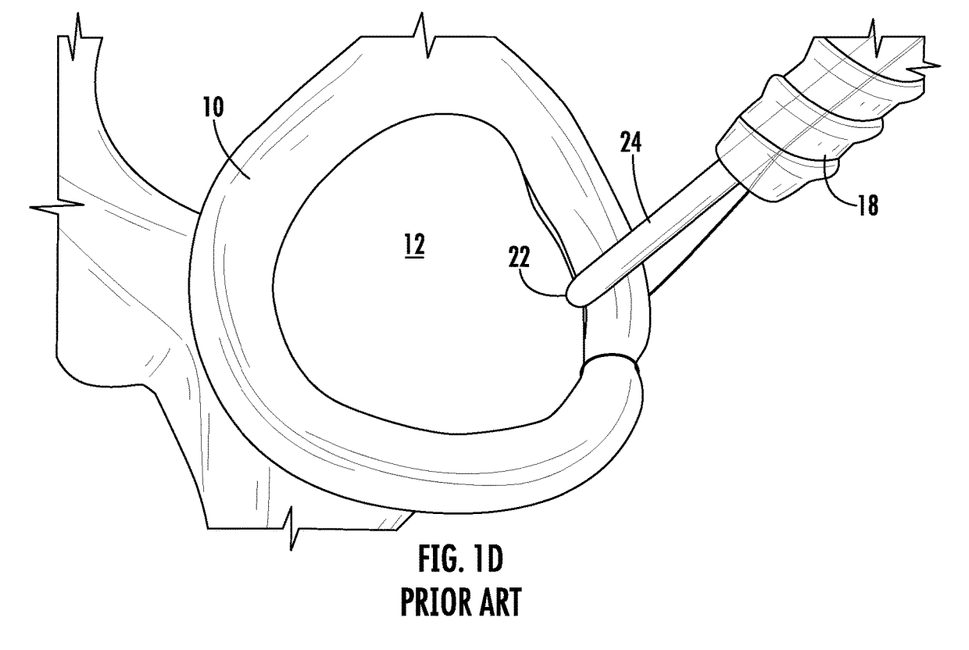
Figure 1E:
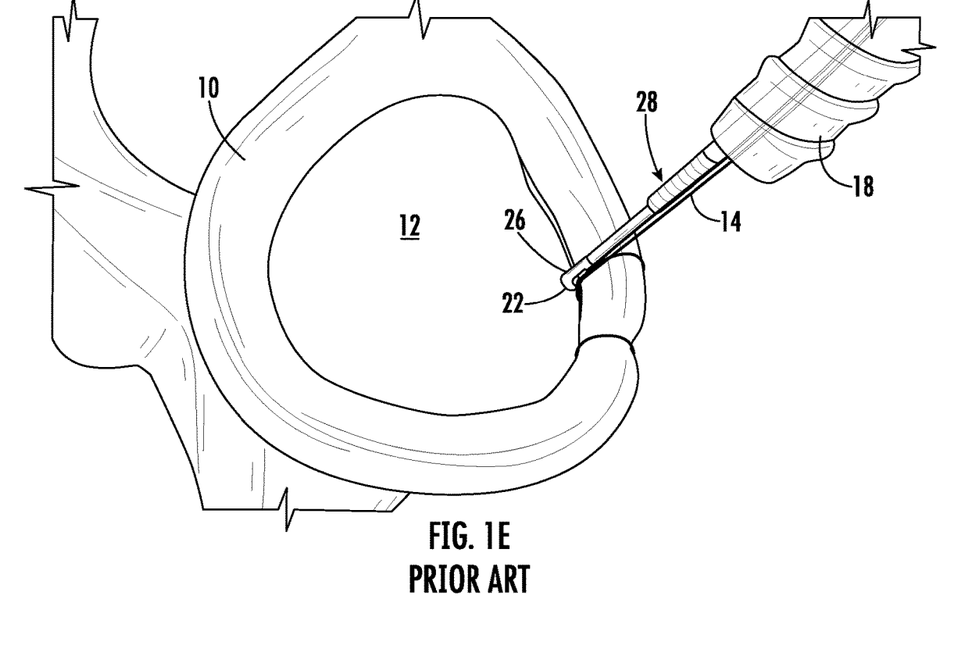

FIGS. 1A-E illustrate a conventional, knotless, suture-first technique for securing a torn shoulder labrum 10 to a glenoid bone 12. In FIG. 1A, the distal end of a conventional straight suture 14 is passed between the labrum 10 and the bone 12 using a suture passing device 16 that has been extended through a posterior cannula 18. After the suture 14 is fed into the joint, the suture passing device 16 is withdrawn, and a grasping instrument 20 is extended through the posterior cannula 18 to grab the suture 14 as shown in FIG. 1B. The distal end of the suture 14 is then drawn into the posterior cannula 18, as shown in FIG. 1C. Next, a socket 22 is formed in the bone 12 using a drill 24 or similar tool extended through the posterior cannular 18, as shown in FIG. 1D. Finally, the distal end of the suture 14 is fed through the distal end 26 of a suture anchor 28, which is then inserted into the bone socket 22, as shown in FIG. 1E. Typically, this procedure is repeated two more times, so that the labrum 10 is secured to the bone 12 at three locations.

Figure 2A:
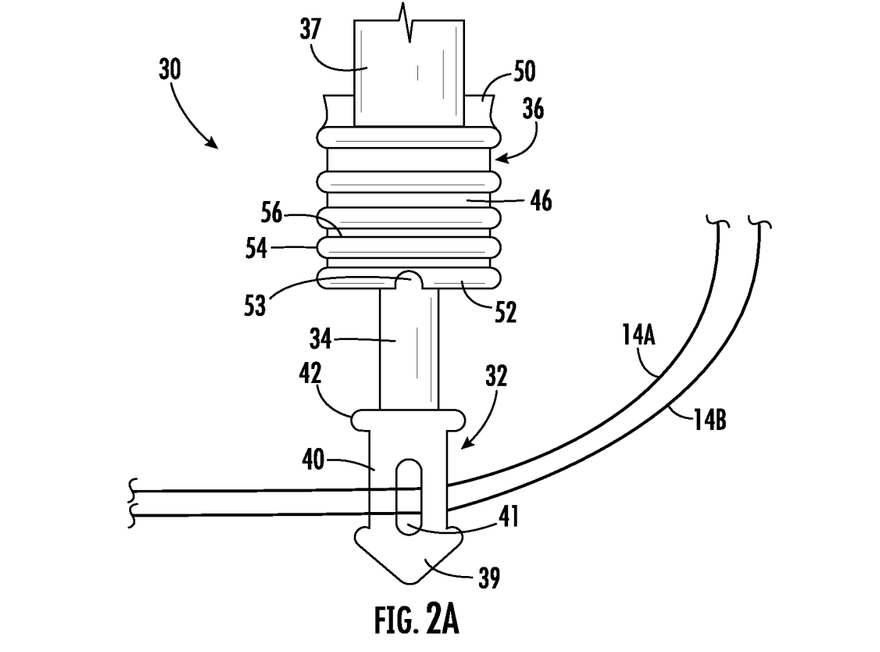
FIG. 2A is a front view of a labral anchor in a pre-deployed configuration.

FIGS. 2A and B show a suture anchor 30 usable in the method of FIGS. 1A-E or other conventional knotless, suture-first, soft tissue-to-bone reattachment methods. The suture anchor 30 comprises a distal tip 32 detachably secured to a distal end of an inner driver shaft 34 that extends through the interior of a proximal anchor body 36. An outer driver shaft 37 is mounted for sliding movement relative to the inner driver shaft 34. The proximal anchor body 36 is detachably secured to and slidable with the distal end of the outer driver shaft 37.

Figure 2B:
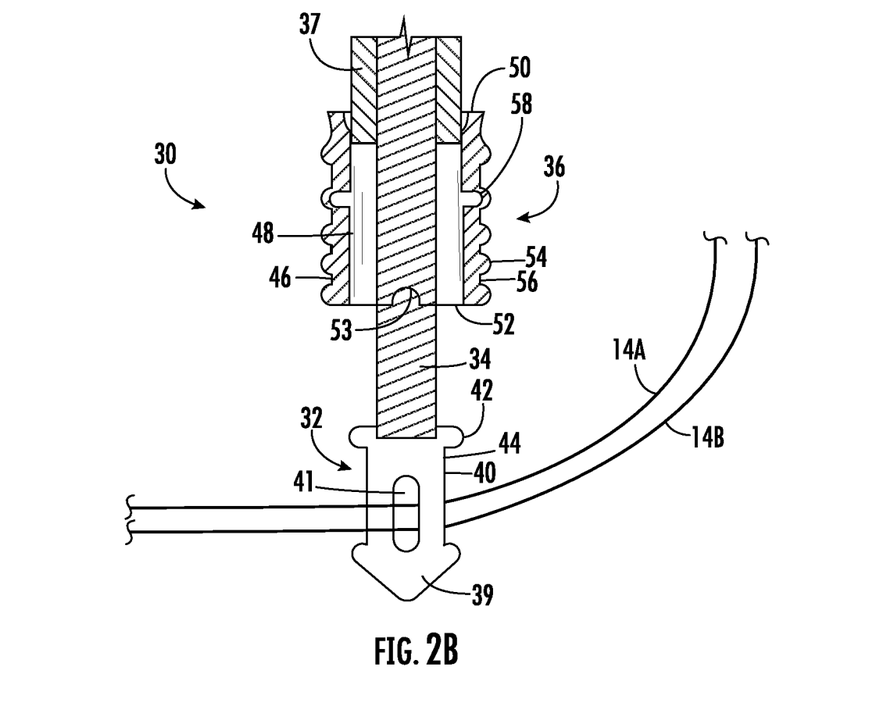
FIG. 2B is a longitudinal sectional view of FIG. 2A.

The distal tip 32 includes an enlarged, rounded distal portion 39 and a proximally extending neck 40 An elongated eyelet 41 formed in the neck 40 is configured to receive the ends of sutures 14A, B. An annular bead 42 extends around the exterior of the proximal end 44 of the neck 38.

The proximal anchor body 36 is tubular in configuration and includes an exterior wall 46, an interior wall 48, a proximal end 50, and a distal end 52 having a semicircular notch 53. The exterior wall 46 comprises a plurality of rounded annular ribs 54 separated by rounded annular channels 56. An annular groove 58 is formed in the interior wall 48 at the proximal end 50.

Figure 3:
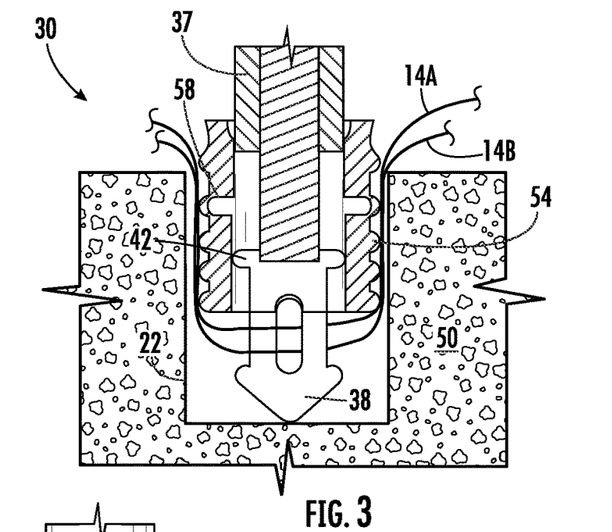
FIG. 3 is a longitudinal sectional view showing the labral anchor of FIGS. 2A and 2B in a partially deployed configuration.
Figure 4A:
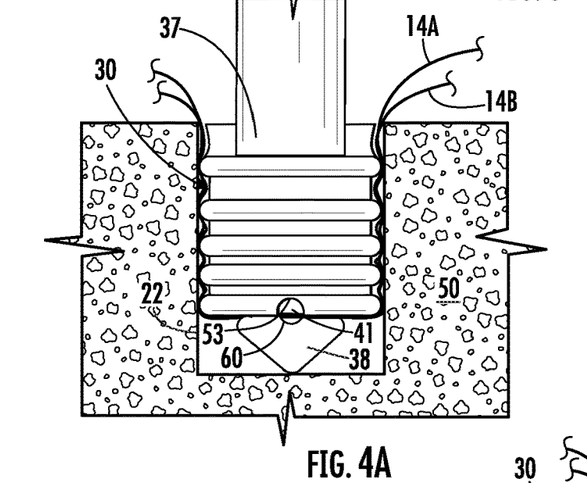
FIG. 4A is a front view of the labral anchor of FIGS. 2A and B in a fully deployed configuration.
Figure 4B:
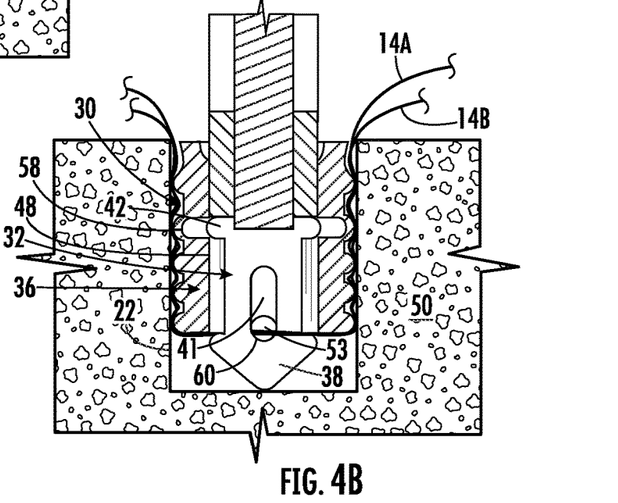
FIG. 4B is a longitudinal sectional view of FIG. 4A.

To secure the sutures 14A,B within a bone 50, a surgeon inserts the distal tip 38 of the suture anchor 30 into a pre-drilled bone socket 22, and pushes down on the outer driver shaft 37, causing the outer driver shaft 37 and proximal anchor body 36 to move together toward the distal tip 38, as shown in FIG. 3. Downward movement of the outer driver shaft 37 and proximal anchor body 36 continues until the annular groove 58 at the proximal end 50 of the proximal anchor body 36 snaps over the annular bead 42 on the neck 40 of the distal tip 36, locking the proximal anchor body 36 and the distal tip 36 together, as shown in FIGS. 4A and 4B. At this point, the outer and inner driver shafts 34, 37 are withdrawn, and the anchor 30 remains in the bone 50, with sutures 14A,B trapped between the ribs 54 of the proximal anchor body 37 and the walls of the bone socket 22, as well as between the distal end 60 of the eyelet 40 and the proximal end of the semicircular notch 53.

Figure 5:
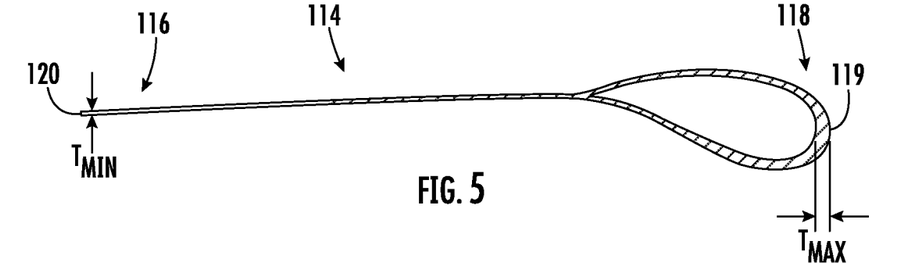
FIG. 5 shows a repair suture.

FIG. 5 shows a repair suture 114 usable in an alternate method for securing torn soft tissue such as a shoulder labrum to a bone such as a glenoid bone. The suture 114 includes a straight end 116 and a looped end 118, and a thickness which varies from a maximum $T_{MAX}$ at the looped end 118 to a minimum $T_{MIN}$ at the straight end 116. In the illustrated embodiment, the thickness tapers gradually from the apex 119 of the looped end 118 to the tip 120 of the straight end 116. However, in another example, the entire looped end 118 may have a constant thickness $T_{MAX}$, and the entire straight end 116 (ie. the entire length of the portion extending from the base of the loop 118 to the tip 120) may have a constant thickness $T_{MIN}$.

Figure 6A:
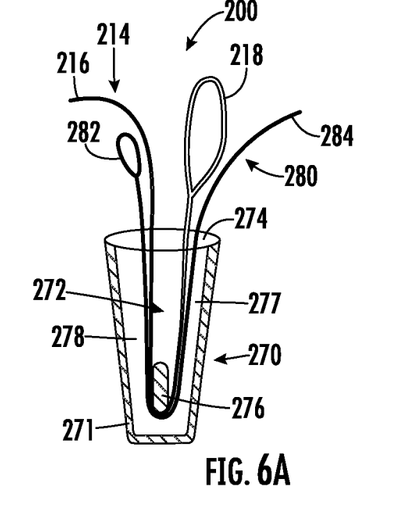
FIG. 6A represents an example of a suture assembly.

FIG. 6A shows a suture assembly 200 comprising a suture anchor 270, a repair suture 214 similar in structure to the repair suture 114 of FIG. 5, and a shuttle suture 280. The suture anchor 270 comprises an inner wall 271 defining a cannulation 272, an open proximal end 274 communicating with the cannulation 272, and a suture engagement feature such as a rod or suture bridge 276 which extends across the cannulation and divides the cannulation into a first side 277 and a second side 278.

The repair suture 214 has been doubled on itself and positioned in the cannulation 272 such that its looped end 218 extends in a proximal direction along the first side 277 of the cannulation 272 and outwardly through the open proximal end 274, and its tail 216 extends in a proximal direction along the second side 278 of the cannulation 272 and outwardly though the open proximal end 274.

The shuttle suture 280 has a looped end 282 and a tail 284, and has been doubled on itself and positioned in the cannulation 272 such that its looped end 282 extends in a proximal direction along the second side 278 of the cannulation 272 and outwardly through the open proximal end 274, and its tail 284 extends in a proximal direction along the first side 277 of the cannulation 272 and outwardly though the open proximal end 274. The looped end 282 of the shuttle suture 280 is smaller than the looped end 218 of the repair suture 214. In addition, the shuttle suture 280 is thinner than the repair suture 214 throughout all or most of its length.

Figure 6B:
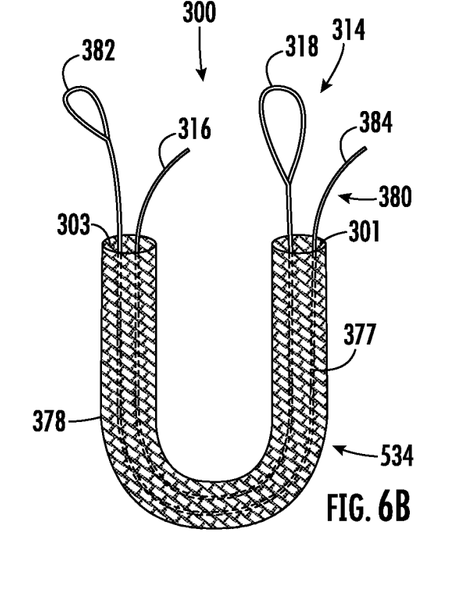
FIG. 6B represents an alternative example of a suture assembly.

FIG. 6B shows an alternate suture assembly 300 including a soft, all suture anchor 370, rather than the hard anchor 270 of FIG. 6A. The repair suture 314 and shuttle suture 380 are woven through or embedded in a collapsible tube or sleeve 286 which is made from the same material as, and may be integral with, the repair suture 314 and shuttle suture 380. The sleeve 386 is bent into a U-shape having a first side 377, a second side 378, and two proximal openings 301, 303. The looped end 318 of the repair suture 314 extends through the first side 377 of the U-shaped sleeve 386 and out the first proximal opening 301, and the straight end 316 of the repair suture 314 extends through the second side 378 of the U-shaped sleeve and out the second proximal opening 303. The looped end 382 of the shuttle suture 380 extends through the second side 378 of the U-shaped sleeve 386 and out the second proximal opening 303, and the tail 384 of the shuttle suture 380 extends through the first side 377 of the U-shaped sleeve 386 and out the first proximal opening 301.

Figure 7:
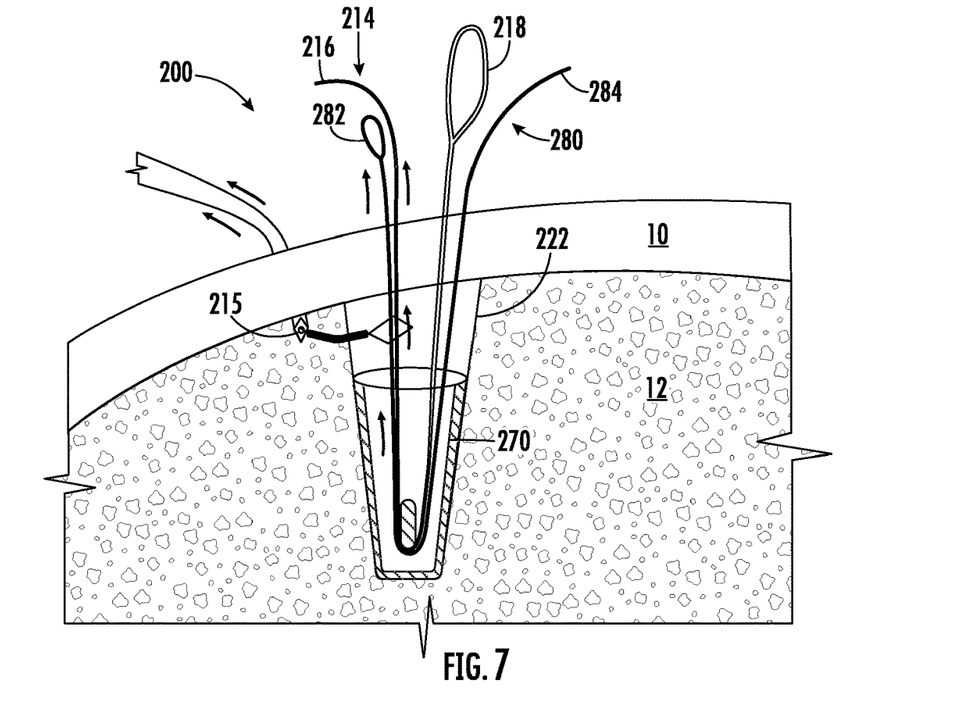
FIGS. 7-12 illustrate a method of securing a torn shoulder labrum to a glenoid bone using the suture assembly of FIG. 6A.
Figure 8:
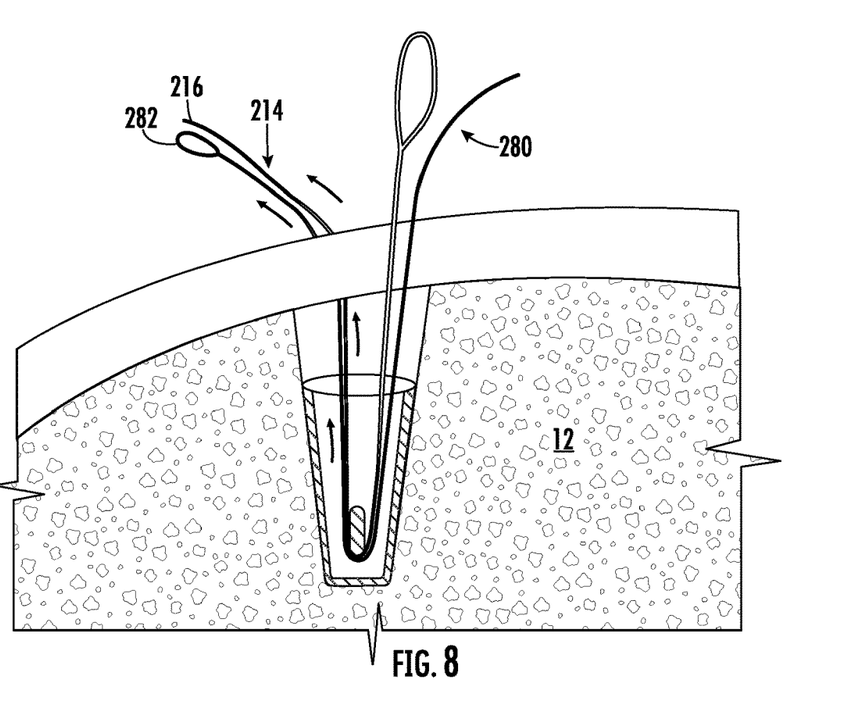
Figure 9:
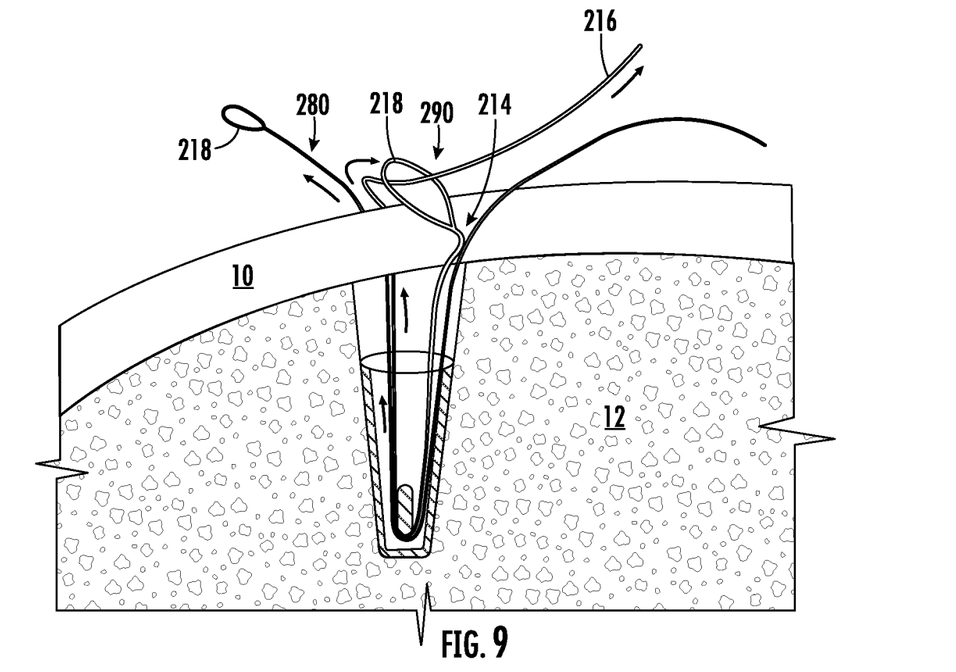
Figure 10:
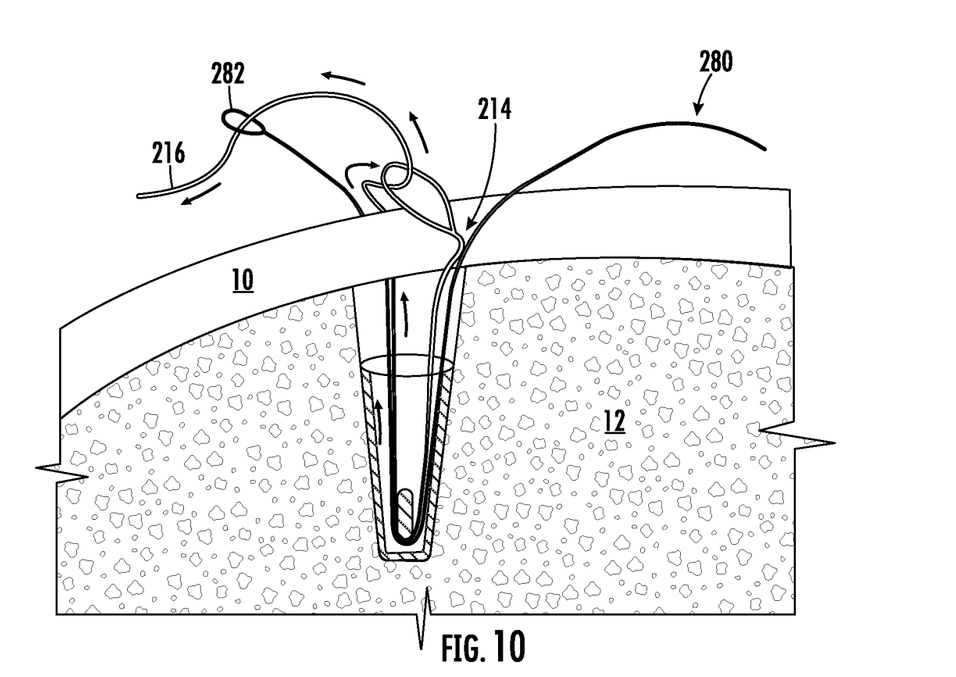
Figure 11:
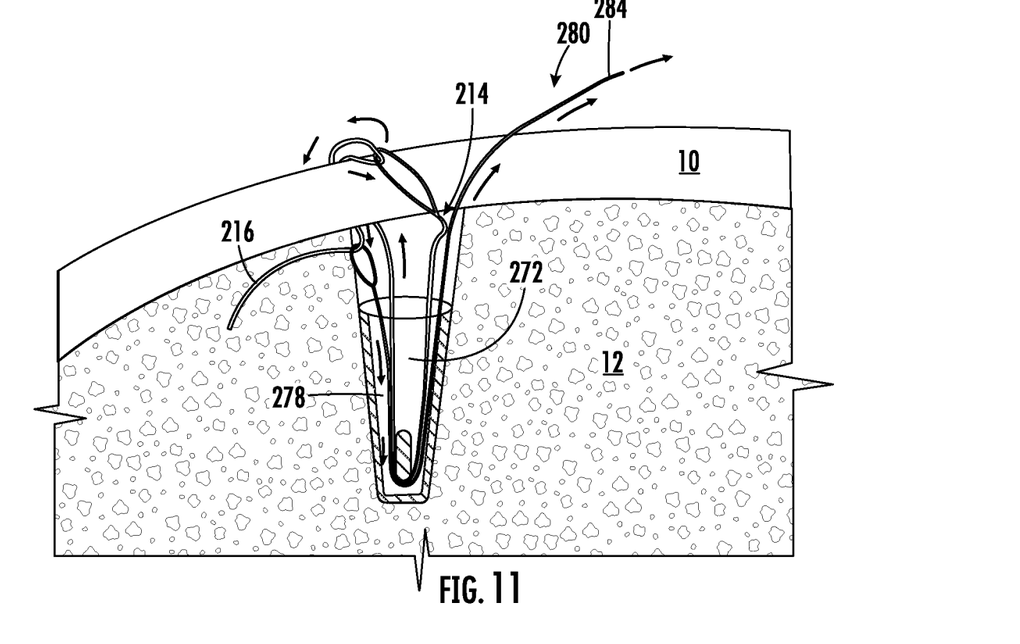
Figure 12:
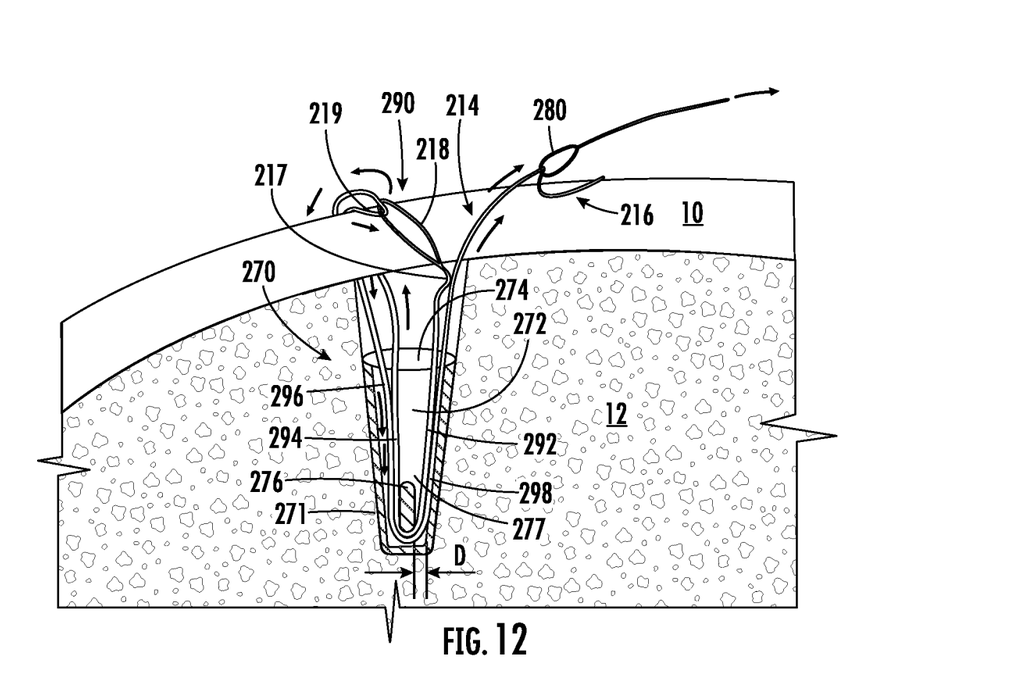

FIGS. 7-12 show a technique for securing soft tissue 10 such as a torn shoulder labrum to a bone 12 such as a glenoid bone using the suture assembly 200 of FIG. 6A. Initially, the suture anchor 270 is inserted in a predrilled socket 222 in the bone 12 at a location to one side of the tissue 10, and a suture passing device 215 is used to pass the tail 216 of the repair suture 214 and the loop 282 of the shuttle suture 280 between the tissue 10 and the bone 12, to the side of the tissue 10 opposite the suture anchor 270, as shown in FIGS. 7 and 8. The tail 216 of the repair suture 214 is then passed back over the tissue 10 and through the looped end 218 of the repair suture to form a luggage tag configuration 290, as shown in FIG. 9. Next, the tail 216 of the repair suture 214 is doubled over itself and drawn through the looped end 282 of the shuttle suture 280, as shown in FIG. 10. The tail 284 of the shuttle suture 280 is then pulled in a proximal direction, drawing the tail 216 of the repair suture 214 down into the second side 278 of the cannulation 272 of the suture anchor, as shown in FIG. 11. Continued pulling of the shuttle suture 280 eventually draws the tail 216 of the repair suture 214 up through the first side 277 of the cannulation 272, and out through the open proximal end 274 of the suture anchor 270, thus tightening the luggage tag configuration 290 against the tissue 10, as shown in FIG. 12. At this point, the shuttle suture 280 may be removed.

In the configuration shown in FIG. 12, the tail 216 of the repair suture 214 can be thought of as comprising four segments: a first segment 292 extending between the base 217 of the loop 218 and the distal end of the suture bridge 276; a second segment 294 extending between the distal end of the suture bridge 276 and the apex 219 of the loop 218 on the second side 278 of the suture bridge 276; a third segment 296 extending between the apex 219 of the loop 218 and the distal end of the suture bridge 276 on the first side 277 of the suture bridge 276; and a fourth segment 298 extending between the distal end of the suture bridge 276 and the looped end 282 of the shuttle suture 280.

The luggage tag configuration 290 is locked into place against the tissue 10 by trapping the segments 292, 294, 296, 298 of the tail 216 of the repair suture 214 in an interference fit between the suture bridge 276 and the inside wall 271 of the suture anchor 279. In order to create this interference fit, the sum of the thicknesses of the first and fourth segments 292, 298 and/or the sum of the thicknesses of the second and third segments 294, 296 should be slightly greater than the distance D between the suture bridge 296 and the inside wall 271 of the suture anchor 279. In the case where the suture tail 216 has a uniform thickness $T_{Min}$ throughout its length and the suture bridge 276 is exactly centered in the cannulation 272, this would mean D should be slightly less than $2T_{MIN}$.

In addition to the shoulder labral repairs described above, the methods and devices disclosed herein may be used to repair dog ears and/or small tears in rotator cuffs, and various other types of injuries in tendons and other soft tissue.

The method of FIGS. 7-12 can also be performed using the all suture anchor of FIG. 6B rather than the hard suture anchor of FIG. 6A. In this case, the luggage tag configuration is locked in place against the tissue by contact force exerted by the all suture anchor on the surrounding bone when the anchor is deployed, rather than by an interference fit between the sutures and an internal suture bridge.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A suture anchor comprising:
    a distal tip configured to be detachably secured to a distal end of a driver shaft, the distal tip including an eyelet configured to receive an end of a repair suture;
    a proximal anchor body mounted for longitudinal movement toward the distal tip; and
    internal locking elements configured to lock the distal tip to the proximal anchor body when the suture anchor is implanted in a bone, wherein the internal elements comprise mating portions of a snap lock including
        a first element formed on a distal portion of the proximal anchor body; and
        a second element formed on a proximal portion of the distal tip.

2. The suture anchor according to claim 1, wherein:
    the first element comprises an annular bead or groove; and
    the second element comprises an annular groove configured to receive the annular bead, or an annular bead configured to project into the annular groove.

3. The suture anchor according to claim 1, further comprising a plurality of annular ribs separated by annular channels formed on an exterior wall of the proximal anchor body.

4. The suture anchor according to claim 1, wherein:
the driver shaft comprises an inner shaft and an outer shaft mounted for sliding movement relative to one another;
the distal tip is configured to be detachably secured to the inner shaft; and
the proximal anchor body is configured to be detachably secured to and slidable with the outer shaft.

5. A suture anchor comprising:
a distal tip configured to be detachably secured to a distal end of a driver shaft, the distal tip including an eyelet configured to receive an end of a repair suture;
a proximal anchor body mounted for longitudinal movement toward the distal tip; and
internal locking elements configured to lock the distal tip to the proximal anchor body when the suture anchor is implanted in a bone;
wherein the proximal anchor body includes a distal end defining a notch configured to align with the eyelet in the distal tip when the proximal anchor body is in a fully deployed position, the notch having a proximal end preventing proximal movement of a repair suture extending through the eyelet when the notch is aligned with the eyelet.

* * * * *